United States Patent
Varani

(10) Patent No.: US 11,622,953 B2
(45) Date of Patent: Apr. 11, 2023

(54) ORAL COMPOSITION FOR THE TREATMENT OF CANKER SORES

(71) Applicant: Antoine Varani, Turlock, CA (US)

(72) Inventor: Antoine Varani, Turlock, CA (US)

(*) Notice: Subject to any disclaimer, the term of this patent is extended or adjusted under 35 U.S.C. 154(b) by 0 days.

(21) Appl. No.: 16/817,515

(22) Filed: Mar. 12, 2020

(65) Prior Publication Data

US 2020/0289452 A1 Sep. 17, 2020

Related U.S. Application Data

(60) Provisional application No. 62/817,203, filed on Mar. 12, 2019.

(51) Int. Cl.
*A61K 31/245* (2006.01)
*A61K 9/00* (2006.01)
*A61K 31/573* (2006.01)

(52) U.S. Cl.
CPC .......... *A61K 31/245* (2013.01); *A61K 9/006* (2013.01); *A61K 31/573* (2013.01)

(58) Field of Classification Search
CPC .... A61K 31/245; A61K 31/573; A61K 47/38; A61K 9/0014; A61K 9/006; A61K 9/06
See application file for complete search history.

(56) References Cited

U.S. PATENT DOCUMENTS

| | | | | |
|---|---|---|---|---|
| 5,362,737 A | * | 11/1994 | Vora | A61K 31/44 514/901 |
| 5,977,087 A | * | 11/1999 | Pehrson, Sr. | A61K 9/0014 514/53 |
| 7,538,082 B2 | * | 5/2009 | Podolsky | A61K 31/33 514/1.1 |
| 9,044,466 B2 | * | 6/2015 | Cohen | A61K 33/30 |
| 2005/0186288 A1 | * | 8/2005 | Chiou | A61K 31/315 424/617 |
| 2019/0175956 A1 | * | 6/2019 | Dolezal | A61K 8/99 |

FOREIGN PATENT DOCUMENTS

WO    WO199609829    *    4/1996

OTHER PUBLICATIONS

The American Academy of Oral Medicine (AAOM, 2007). (Year: 2007).*

* cited by examiner

*Primary Examiner* — Umamaheswari Ramachandran

(74) *Attorney, Agent, or Firm* — Kilpatrick Townsend & Stockton LLP

(57) ABSTRACT

A composition, and method for using the same, for treating a canker sore includes 10-30% of an ester local anesthetic, 0.5-2% of a corticosteroid, and a carrier for the ester local anesthetic and the corticosteroid. The carrier is formulated as a paste so as to be applied topically to the canker sore to deliver the ester local anesthetic and the corticosteroid simultaneously to the canker sore.

10 Claims, No Drawings

ORAL COMPOSITION FOR THE TREATMENT OF CANKER SORES

CROSS REFERENCE TO RELATED APPLICATIONS

This application claims the benefit of U.S. Provisional Application No. 62/817,203, filed Mar. 12, 2019, and entitled "Oral Composition for the Treatment of Canker Sores", the entirety of which is hereby incorporated by reference herein.

BACKGROUND

Canker sores, also called aphthous ulcers, are small shallow lesions that develop on the soft tissue of the mouth or at the base of gums. Canker sores, unlike cold sores, are not associated with the herpes virus. The cause of canker sores is not really known, and it is believed that outbreaks can be attributed to a number of reasons, including emotional stress. Canker sores can include inflamed tissue in the mouth or gums, and can be quite painful.

Substances for treating canker sores topically focus on the need to relieve pain through a local anesthetic. Several examples include Orajel® (20% benzocaine); Ulcerease® (0.6% phenol); Ziklactin-B® (10% benzocaine); Kank-A (20% benzocaine); Cankaid (20% benzocaine); and Anbesol® (20% benzocaine). While these anesthetic-based solutions address pain, they lack any component to address inflammation.

Compositions that have focused on reducing inflammation from topical dermatoses typically use a 0.1% triamcinolone acetonide composition, and is sold under the name Kenalog Orabase®. While this product includes a corticosteroid, the composition lacks an anesthetic. This and other corticosteroids, such as hydrocortisone, take time to yield beneficial effects of reducing inflammation, and a quick removal of the corticosteroid from a desired site could render the composition useless. Further, without a local anesthetic, application of such an inflammation-reducing-only composition can be quite painful.

Almost all conventional canker sore treatments employ a gel-based carrier that covers the sore but quickly dries up, allowing any beneficial component of the composition to quickly wash away with saliva.

There remains a need for a canker sore treatment that is capable of delivering an anesthetic and an anti-inflammatory effective for relieving pain and inflammation associated with canker sores, respectively, and which will not quickly dissipate or wash away in a saliva-flushed environment of the mouth.

SUMMARY

The present invention relates to a composition and a method for treating a canker sore. The treatment involves topical administration of a treatment composition. The treatment composition includes an anesthetic substance, an anti-inflammatory substance, and a carrier substance to carry and apply the anesthetic substance and the anti-inflammatory substance directly to a canker sore.

In preferred exemplary implementations, the composition includes 10-30% benzocaine; 0.5-2% hydrocortisone; and a paste carrier, where the treatment composition, when applied topically, delivers benzocaine and hydrocortisone to the canker sore. In order to resist quick drying and/or washing away from the canker sore site, the paste carrier may include sodium carboxymethylcellulose, gelatin, citrus, pectin, petrolatum, and titanium dioxide. In a specific implementation, the carrier may also comprise vanillin. Depending on the exact amount of benzocaine and/or hydrocortisone, the treatment composition is deliverable as a paste.

The details of one or more embodiments are set forth in the accompanying drawings and the description below. Other features and advantages will be apparent from the description and drawings, and from the claims.

DETAILED DESCRIPTION

This document describes a composition, and a method of using the composition, for treating a canker sore. The treatment involves topical administration of a treatment composition that is provided as a paste. The treatment composition includes an anesthetic substance, an anti-inflammatory substance, and a carrier substance to carry and apply the anesthetic substance and the anti-inflammatory substance directly to a canker sore.

In some implementations, a composition for treating a canker sore includes 10-30% of an ester local anesthetic, 0.5-2% of a corticosteroid, and a carrier for the ester local anesthetic and the corticosteroid. The carrier is formulated as a paste so as to be applied topically to the canker sore to deliver the ester local anesthetic and the corticosteroid to the canker sore. The paste is formulated to withstand salivary pressure in inhibit washing away of the composition from the canker sore site.

In some implementations, a method for treating a canker sore includes applying topically, and directly to the canker sore, a treatment composition comprising benzocaine, hydrocortisone, and a paste carrier.

In some preferred implementations, the treatment composition includes between 10-30% benzocaine and 0.5-2% hydrocortisone. Preferably the composition includes about 20% benzocaine and about 1% hydrocortisone. The paste carrier can include one or more of, without limitation, sodium carboxymethylcellulose, gelatin, citrus, pectin, petrolatum, and titanium dioxide. The paste carrier may also optionally include vanillin, which can provide a pleasant taste in the mouth of a patient and minimize production of saliva.

Through experimentation it has been found that using an anesthetic in combination with the hydrocortisone works particularly well to heal canker sores because patients normally fidget with the canker sore in the mouth (e.g., with their tongue or with an external object, typically a hard or brittle object). This action by the patient: (1) irritates the canker sore further; and (2) removes (i.e., licks off) the hydrocortisone before the medication has completely carried out its effect. By adding in the anesthetic, the patient is less likely to fidget with that area and, in turn, less likely to irritate or lick off the hydrocortisone, allowing the composition to heal the canker sore quicker.

By applying the medication or composition as disclosed herein, it has been found that lesions generally shrank to half their size with less swelling and irritation within 24 hours of application. The duration of these lesions is approximately 7-14 days when untreated. By avoiding the removal of hydrocortisone, the cycle causing the lesions to last for up to two weeks can be avoided. Further, the medication maintains an adhesive property that tolerates saliva and allows the treatment effect of the medication to persist after application to the canker sore.

A medicament that includes the composition of the present disclosure can be applied in a small amount sufficient to completely cover the lesions. In a particular implementation of a method, the medicament is applied using a cotton swab such as a Q-Tip®. The cotton head of a swab resembles the size of most canker sores, thus providing an optimal size applicator for treatment of canker sores. The composition is blotted by the cotton swab and then spread over the canker sore. In another implementation, the composition is supplied in a tube with a long neck, allowing the user to easily reach the cheeks and back of the tongue of the patient.

When the composition is applied in this manner, the patient will be free to eat or drink within one minute of applying the composition. The medication of the present composition can be applied twice daily. In severe cases, the medication may be applied once every eight hours, and the paste carrier will ensure a longer application (longer than several minutes, i.e. longer than 5 minutes) of the medication than other medical compositions, in order to allow the components of the composition to work effectively.

Example 1

The treatment composition of this example includes 20% benzocaine, 1% hydrocortizone, sodium carboxymethyl cellulose, gelatin, citrus, pectin, petrolatum, and titanium dioxide. The composition is prepared by mixing each of the above ingredients until a smooth and uniform paste composition is obtained.

Example 2

The composition of Example 1 was applied directly to a patient's canker sore on the inside of the lip. After 24 hours, the lesion had shrunk to half of its size. Accordingly, a composition as described herein greatly speeds up the healing process for canker sores in a patient.

Although a few embodiments have been described in detail above, other modifications are possible. Other embodiments may be within the scope of the following claims.

The invention claimed is:

1. A composition for treating a canker sore in the mouth or at the base of the gums of a patient, the composition comprising:
   10-30% of an ester local anesthetic;
   0.5-2% of a corticosteroid; and
   a carrier for the ester local anesthetic and the corticosteroid, the carrier being formulated as a paste to withstand salivary pressure and to be applied topically to the canker sore to deliver and apply the ester local anesthetic and the corticosteroid to the canker sore, the carrier comprising vanillin to minimize production of saliva by the patient when the ester local anesthetic and the corticosteroid are applied to the canker sore, wherein the carrier is configured to maintain application of the ester local anesthetic and the corticosteroid to the canker sore for more than five minutes and wherein the corticosteroid is hydrocortisone.

2. The composition in accordance with claim 1, wherein the ester local anesthetic comprises benzocaine.

3. The composition in accordance with claim 1, wherein the composition includes about 20% of the ester local anesthetic.

4. The composition in accordance with claim 1, wherein the composition includes about 1% of the corticosteroid.

5. The composition in accordance with claim 1, wherein the carrier further comprises one or more of sodium carboxymethylcellulose, gelatin, pectin, petrolatum, and titanium dioxide.

6. A composition for treating a canker sore in the mouth or at the base of the gums of a patient, the composition comprising:
   an ester local anesthetic;
   a corticosteroid; and
   a carrier for the ester local anesthetic and the corticosteroid, the carrier being formulated as a paste to withstand salivary pressure and to be applied topically to the canker sore to deliver the ester local anesthetic and the corticosteroid simultaneously to the canker sore, and to maintain delivery of the ester local anesthetic and corticosteroid to the canker sore for more than five minutes, the carrier comprising an amount of vanillin sufficient to minimize production of saliva by the patient when the ester local anesthetic and the corticosteroid are applied to the canker sore and wherein the corticosteroid is hydrocortisone.

7. The composition in accordance with claim 6, wherein the ester local anesthetic comprises benzocaine.

8. The composition in accordance with claim 6, wherein the composition includes about 20% of the ester local anesthetic.

9. The composition in accordance with claim 6, wherein the composition includes about 1% of the corticosteroid.

10. The composition in accordance with claim 6, wherein the carrier further comprises one or more of sodium carboxymethylcellulose, gelatin, pectin, petrolatum, and titanium dioxide.

\* \* \* \* \*